(12) United States Patent
Dekany et al.

(10) Patent No.: US 8,796,434 B2
(45) Date of Patent: Aug. 5, 2014

(54) CRYSTALLINE CARBOHYDRATE DERIVATIVE

(75) Inventors: Gyula Dekany, Sinnamon Park (AU); Károly Ágoston, Telki (HU); István Bajza, Debrecen (HU); Marie Bøjstrup, Tåstrup (DK); Ignacio Fegueroa Pérez, Miami, FL (US); Lars Kröger, Hamburg (DE); Christoph H. Röhrig, Mühlingen (DE)

(73) Assignee: Glycom A/S, KGS. Lyngby (DK)

( * ) Notice: Subject to any disclaimer, the term of this patent is extended or adjusted under 35 U.S.C. 154(b) by 574 days.

(21) Appl. No.: 13/054,314

(22) PCT Filed: Jul. 15, 2009

(86) PCT No.: PCT/EP2009/059059
§ 371 (c)(1),
(2), (4) Date: Mar. 25, 2011

(87) PCT Pub. No.: WO2010/007090
PCT Pub. Date: Jan. 21, 2010

(65) Prior Publication Data
US 2011/0166339 A1  Jul. 7, 2011

(30) Foreign Application Priority Data
Jul. 15, 2008  (GB) .................................. 0812895.1

(51) Int. Cl.
| C07H 5/04 | (2006.01) |
| C07H 5/06 | (2006.01) |
| C08B 37/00 | (2006.01) |
| C07H 1/00 | (2006.01) |
| C07H 1/06 | (2006.01) |
| C07H 1/08 | (2006.01) |

(52) U.S. Cl.
USPC .......................... 536/18.7; 536/1.11; 536/127

(58) Field of Classification Search
CPC .............. C07H 3/04; C07H 5/06; C07H 1/06; C07H 1/00
USPC ........................................ 536/1.11, 18.7, 127
See application file for complete search history.

(56) References Cited

FOREIGN PATENT DOCUMENTS

| AT | 503 400 A1 | 10/2007 |
| JP | H06-056867 | 3/1994 |
| JP | H10-072483 | 3/1998 |
| JP | 2004-352673 | 12/2004 |
| JP | 2008-515968 | 5/2008 |
| WO | 2006/070985 | 7/2006 |
| WO | WO 2007/104311 | 9/2007 |

OTHER PUBLICATIONS

Derwent Accession No. 2008-M33803. English translation of abstract for AT 503 400 A1 (2007).*
Armstrong, D.W., Jin, H.L. (1989) Liquid Chromatographic Separation of Anomeric Forms of Saccharides With Cyclodextrin Bonded Phases. Chirality, vol. 1, p. 27-37.*
International Search Report as issued for PCT/EP2009/059059, dated Jan. 27, 2010.
English Translation of Abstract for Austrian Patent No. AT 503 400 A1, dated Oct. 15, 2007.
Arnold E. Stütz et al., "An Exceptionally Simple Chemical Synthesis of O-Glycosylated d-Glucosamine Derivatives by Heyns Rearrangement of the Corresponding O-Glycosyl Fructoses," Journal of Carbohydrate Chemistry, vol. 22, No. 5, pp. 253-265 (2003).
Jianwen Fang et al., "A Unique Chemoenzymatic Synthesis of α-Galactosyl Epitope Derivatives Containing Free Amino Groups: Efficient Separation and Further Manipulation," J. Org. Chem., vol. 64, No. 11, pp. 4089-4094 (1999).
Tanja M. Wrodnigg et al., "The Heyns Rearrangement Revisited: An Exceptionally Simple Two-Step Chemical Synthesis of D-Lactosamine from Lactulose," Angew. Chem. Int. Ed., vol. 38, No. 6, pp. 827-828 (1999).
Jianwen Fang et al., "Chemical and Enzymatic Synthesis of Glycoconjugates 3: Synthesis of Lactosamine by Thermophilic Galactosidase Catalyzed Galactosylation on a Multigram Scale," Tetrahedrom Letters, vol. 39, No. 9, pp. 919-922 (1998).
Richard Kuhn et al., "Synthesis of 2-acetamidolactose," University Heidelberg, Germany, Chemische Berichte, vol. 87, pp. 1547-1552 (1954).
Japanese Office Action mailed Nov. 12, 2013 in corresponding Japanese Patent Application No. 2011-517916.
Chinese Search Report dated Aug. 28, 2013 in corresponding Chinese Patent Application No. 200980127547.5.
Chinese Office Action dated Oct. 21, 2013 in corresponding Chinese Patent Application No. 200980127547.5.
Shiyong Zhu et al., "Gas Chromatography for Derivatives," First Edition, A Chapter of "3. Separation of Inseparable Substance Pair," published only in Chinese, 32 pages with Concise Statement of Relevance (Feb. 28, 1993).

* cited by examiner

*Primary Examiner* — Scarlett Goon
(74) *Attorney, Agent, or Firm* — Pillsbury Winthrop Shaw Pittman LLP

(57) ABSTRACT

α-Lactosamine hydrochloride, substantially free of β-lactosamine hydrochloride; a method of preparing α-lactosamine hydrochloride monohydrate from an anomeric mixture of lactosamine hydrochloride, including: preparing a solution including the anomeric mixture of lactosamine hydrochloride, water and at least one water-miscible organic solvent at a temperature of 0-100° C., and cooling the solution to cause crystallization of α-lactosamine hydrochloride monohydrate; a method of preparing anhydrous α-lactosamine hydrochloride; and use of α-lactosamine hydrochloride as a food supplement or intermediate in synthesis.

5 Claims, 3 Drawing Sheets

*Crystal data*

$C_{12}H_{26}Cl_1N_1O_{11}$
$M_r = 395.79$
Monoclinic, $P2_1$
$a = 4.7931\ (8)$ Å
$b = 13.5508\ (19)$ Å
$c = 13.2816\ (19)$ Å
$\beta = 93.970\ (10)°$ $V = 860.6\ (2)$ Å$^3$
$Z = 2$
Cu $K\alpha$
$\mu = 2.52$ mm$^{-1}$
$T = 433\ (2)$ K
$0.08 \times 0.05 \times 0.02$ mm

*Data collection*

Multiwire proportional diffractometer
Absorption correction: none
6882 measured reflections
2509 independent reflections
1793 reflections with $I > 2\sigma(I)$ $R_{int} = 0.098$

*Refinement*

$R[F^2 > 2\sigma(F^2)] = 0.061$ $wR(F^2) = 0.156$ $S = 1.03$ 2509 reflections 254 parameters 10 restraints H atoms treated by a mixture of independent and constrained refinement
$\Delta\rho_{max} = 0.33$ e Å$^{-3}$
$\Delta\rho_{min} = -0.33$ e Å$^{-3}$
Absolute structure: Flack H D (1983), Acta Cryst. A39, 876-881
Flack parameter: 0.02 (4)

*Hydrogen-bond geometry (Å, °)*

| D—H···A | D—H | H···A | D···A | D—H···A |
|---|---|---|---|---|
| N12—H12B···O11 | 0.89 | 2.34 | 2.788 (7) | 111 |
| N12—H12B···O1W$^i$ | 0.89 | 2.36 | 3.157 (9) | 150 |
| N12—H12C···O4$^{ii}$ | 0.89 | 2.24 | 2.930 (7) | 134 |
| N12—H12C···O13 | 0.89 | 2.46 | 2.876 (8) | 109 |
| N12—H12C···O3$^{ii}$ | 0.89 | 2.32 | 2.857 (8) | 119 |
| N12—H12D···O1W$^{iii}$ | 0.89 | 1.96 | 2.828 (9) | 165 |
| O13—H13···O5 | 0.90 (4) | 1.92 (5) | 2.738 (7) | 150 (7) |
| O13—H13···O6 | 0.90 (4) | 2.57 (6) | 3.269 (6) | 135 (6) |
| O16—H16···Cl1 | 0.91 (4) | 2.23 (4) | 3.139 (6) | 173 (7) |
| O2—H2···O6$^{iv}$ | 0.91 (4) | 2.40 (7) | 2.728 (7) | 101 (5) |
| O3—H3···O13$^{iv}$ | 0.88 (4) | 1.85 (4) | 2.704 (7) | 163 (7) |
| O4—H4···Cl1$^{ii}$ | 0.91 (4) | 2.18 (4) | 3.085 (5) | 173 (7) |
| O6—H6···O2$^v$ | 0.93 (4) | 1.83 (4) | 2.728 (7) | 161 (7) |
| O11—H11···O15$^{vi}$ | 0.89 (4) | 3.01 (7) | 3.252 (7) | 97 (5) |
| O1W—H1W···O16$^{vii}$ | 0.92 (2) | 1.84 (2) | 2.754 (8) | 175 (7) |
| O1W—H2W···Cl1 | 0.91 (2) | 2.45 (3) | 3.344 (6) | 167 (7) |

Symmetry codes: (i) $x-1, y+1, z$; (ii) $-x+1, y+1/2, -z+1$; (iii) $x, y+1, z$; (iv) $-x+2, y-1/2, -z+1$; (v) $-x+2, y+1/2, -z+1$; (vi) $x-1, y, z$; (vii) $-x+2, y-1/2, -z+2$.

Figure 2

CRYSTALLINE CARBOHYDRATE DERIVATIVE

CROSS REFERENCE TO RELATED APPLICATIONS

This application is the U.S. National Phase of PCT/EP2009/059059, filed Jul. 15, 2009, which claims priority to Great Britain Patent Application No. 0812895.1, filed Jul. 15, 2008. The content of all of these applications are incorporated herein by reference in their entirety.

FIELD OF THE INVENTION

The present invention provides crystalline α-lactosamine hydrochloride monohydrate, and methods of making this compound.

BACKGROUND OF THE INVENTION

Oligosaccharides have several structural forms due to their polyhydroxy character and their terminal carbonyl functions. Both aldoses and ketoses can be present in pyranose, furanose and open chain forms. Furthermore, hemiacetals/hemiketals of oligosaccharides can be characterized by both α and β anomeric linkages. The above described structural diversity makes the isolation of mono and oligosaccharides as a single chemical entity difficult. Selective crystallization of anomeric mixtures of carbohydrates can be rather difficult and quite frequently both anomers are present in crystal structures. Such difficulties often prevent the purification of important carbohydrates via crystallization. The present invention provides a facile approach for the purification of lactosamine hydrochloride via anomer selective crystallization.

Lactosamine hydrochloride is an essential disaccharide present in many natural oligosaccharide structures. To the best knowledge of the present inventors, the single anomeric form of α-lactosamine hydrochloride has never previously been synthesized and characterized. To date, only the anomeric mixture of lactosamine hydrochloride has been prepared, either via chromatography or precipitationt.[1-6] The characterization of lactosamine hydrochloride has been rather modest in these publications due to the nature of the anomeric mixture of products. Such lactosamine hydrochloride products have always been described as inseparable anomeric mixtures containing both α and β anomers.

The very first methodology providing anomeric mixtures of lactosamine hydrochloride via crystallization has been described recently.[7] The resulting product has been characterized by 1H and 13C NMR. The anomeric mixture nature of the product was indicated by the following characteristic chemical shifts: $^1$H NMR (D$_2$O) δ=5.23 (d, 1H, H-1α, $J_{1,2}$=3.1 Hz); δ=4.75 (d, 0.4H, H-1β, $J_{1,2}$=8.43 Hz); $^{13}$C NMR (D$_2$O) δ=103.13 (C-1' β), 103.08 (C-1' α), 92.67 (C-1α), 88.99 (C-1β).

An Austrian patent application also describes the precipitation/crystallization approach, also providing an anomeric mixture of lactosamine hydrochloride.[8] The described process gave lactosamine hydrochloride as an inseparable mixture containing 60% α- and 40% β-lactosamine hydrochloride proven by the chemical shifts of the two different chemical entities $^1$H NMR (D$_2$O) (δ=5.28 (d, 0.6H, H-1α, $J_{1,2}$=3.6 Hz); δ=4.81 (d, 0.4H, H-1β, $J_{1,2}$=8.6 Hz).

The present invention provides crystalline α-lactosamine hydrochloride monohydrate as a single chemical entity, as demonstrated by X-ray crystallography and $^1$H NMR spectroscopy. Furthermore, the present invention provides anomer selective crystallization methods for lactosamine hydrochloride producing exclusively α-lactosamine hydrochloride monohydrate. No β-lactosamine hydrochloride could be detected in the crystalline product using the most powerful analytical methodologies. The present invention has a great commercial value in large scale production of lactosamine hydrochloride providing high purity of product, which cannot be achieved by any other known purification methods.

Accordingly, the first aspect of the present invention provides α-lactosamine hydrochloride, as shown in Formula 2, substantially free of β-lactosamine hydrochloride.

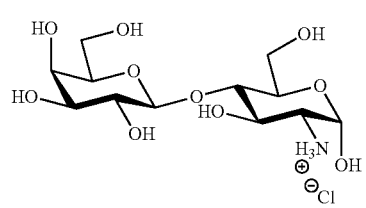

Formula 2

This product has never previously, to the best knowledge of the present inventors, been prepared and characterized. Preferably, the α-lactosamine hydrochloride comprises less than 5 wt % of β-lactosamine hydrochloride, such as less than 2 wt %, preferably less than 1 wt %, such as 0.5 wt %, and most preferably less than 0.1 wt %.

The present inventors have selectively crystallised the α-form from an anomeric mixture of lactosamine hydrochloride, and have confirmed the identity of the crystalline product to be α-lactosamine hydrochloride monohydrate by means of X-ray crystallography. In addition, the present inventors have prepared anhydrous α-lactosamine hydrochloride.

Anhydrous α-lactosamine hydrochloride having a water content within 0-1% by weight can be made from α-lactosamine hydrochloride monohydrate by removing water of crystallisation via several methods known in the art, such as heating α-lactosamine hydrochloride monohydrate, preferably in vacuum and/or in the presence of a dessicant.

The second aspect of the present invention provides a method of preparation of α-lactosamine hydrochloride monohydrate from an anomeric mixture of lactosamine hydrochloride, comprising:

preparing a solution comprising the anomeric mixture of lactosamine hydrochloride, water and at least one water-miscible organic solvent at a temperature of 0-100° C.;
cooling the solution to cause crystallisation of α-lactosamine hydrochloride monohydrate.

Suitably, the solution is prepared by dissolving the anomeric mixture of lactosamine hydrochloride in water at a temperature of 40-100° C., and subsequently adding the at least one water miscible organic solvent.

Suitably, the method may further comprise the preliminary steps of: dissolving the anomeric mixture of lactosamine hydrochloride in water; and adding the solution to a much larger volume of acetone, such as a tenfold volume of acetone compared with the volume of the aqueous solution, to cause precipitation of a white powder, which powder is then used as the anomeric mixture in preparing the solution comprising the anomeric mixture, water and at least one water miscible organic solvent. This preliminary step forms an acetone adduct of the anomeric mixture that is insoluble in this water/ acetone mixture, and so precipitates as a white powder leaving other impurities in solution.

Suitably, the at least one water miscible organic solvent is selected from the group consisting of acetone, tetrahydrofuran, acetonitrile, dioxane, aliphatic alcohols, and 1,2-dimethoxyethane. Suitably, where acetone is used as the at least one water-miscible solvent, the volume of acetone in the solvent mixture is much less than that used to create the acetone adduct, such as up to around 2-3 times the volume of the water in the solvent mixture.

Suitably, the at least one water-miscible solvent is used in greater volume than the volume of water used. Suitably, the water miscible solvent is present at least twice the volume of water used, such as at least 2.5 or 3 times the amount of water used.

Preferably, the at least one water miscible organic solvent is at least one aliphatic alcohol ROH, wherein R is selected from methyl, ethyl, isopropyl, isobutyl and n-butyl. Preferably, the at least one aliphatic alcohol is isopropyl alcohol or isobutyl alcohol. Most preferably, isopropyl alcohol is used.

Preferably, the solution is cooled to between −5 and 30° C. in order to cause crystallisation. Preferably, the solution may be stirred during cooling in order to prevent the formation of large crystals that can capture impurities. This is particularly preferred when crystallising α-lactosamine hydrochloride on a large scale, as the formation of very large crystals in the absence of stirring can cause handling problems and damage to parts of the crystallisation vessel when the crystals are recovered from the vessel. Methods of inducing crystallisation known to the skilled man may also be employed, such as scratching the side of the crystallisation vessel with a glass rod, or providing a seed crystal in the crystallisation vessel. It is particularly preferred to use a seed crystal to induce crystallisation, as this provides better crystal purity and more rapid crystallisation, and the seed crystal used is preferably a crystal of α-lactosamine hydrochloride monohydrate made according to the method of the invention.

The purity of the starting anomeric mixture of lactosamine hydrochloride can vary from 5%-100% of the α-anomer.

The third aspect of the present invention provides a method of preparation of α-lactosamine hydrochloride monohydrate from lactosamine, comprising:
dissolving lactosamine in an aqueous hydrochloric acid solution at 40-100° C.: and
cooling the solution to cause crystallization of the α-lactosamine hydrochloride monohydrate.

Suitably, the concentration of aqueous HCl solution may vary from 0.1% to 38%.

Preferably, the aqueous HCl solution comprises at least one water miscible organic solvent. Suitably, organic solvents such as acetone, tetrahydrofuran, acetonitrile, dioxane, methanol, ethanol, propanol, butanol, or 1,2-dimethoxyethane may be comprised in the aqueous HCl solution. Preferably, the at least one water miscible organic solvent is at least one aliphatic alcohol ROH, wherein R is selected from methyl, ethyl, isopropyl, isobutyl and n-butyl. More preferably, the at least one aliphatic alcohol is isopropyl alcohol or isobutyl alcohol. Most preferably, the at least one aliphatic alcohol is isopropyl alcohol.

Suitably, the solution is cooled to between −5 and 30° C. in order to cause crystallisation. Preferably, the solution may be stirred during cooling in order to prevent the formation of large crystals that can capture impurities. As mentioned above, this is particularly preferred when performing the crystallisation on a large scale. Methods of inducing crystallisation known to the skilled man may also be employed, such as scratching the side of the crystallisation vessel with a glass rod, or providing a seed crystal in the crystallisation vessel. It is particularly preferred to provide a seed crystal to induce crystallisation, as this provides better crystal purity and more rapid crystallisation, and the seed crystal used is preferably a crystal of α-lactosamine hydrochloride monohydrate made according to the method of the invention.

The fourth aspect of the present invention provides a method of preparing anhydrous α-lactosamine hydrochloride having a water content of from 0 to 1% by weight, comprising heating α-lactosamine hydrochloride monohydrate to cause thermal removal of substantially all of the water of crystallisation.

Suitably, the heating temperature can vary from 20-172° C.

Preferably, the method comprises heating the monohydrate under vacuum. Suitably, the method may comprise the use of a dessicant to assist with removal of water of crystallisation.

The present invention further comprises the use of α-lactosamine hydrochloride which is substantially free of β-lactosamine hydrochloride in a food product or beverage, or as a functional food supplement.

The present invention further comprises the use of α-lactosamine hydrochloride which is substantially free of β-lactosamine hydrochloride as an intermediate/precursor for organic synthesis, in particular in the synthesis of human milk oligosaccharides.

BRIEF DESCRIPTION OF THE FIGURES

FIG. 2 shows the data obtained from X-ray diffraction studies of α-lactosamine hydrochloride monohydrate.

DETAILED DESCRIPTION OF THE INVENTION

General Procedure

Figure 1:
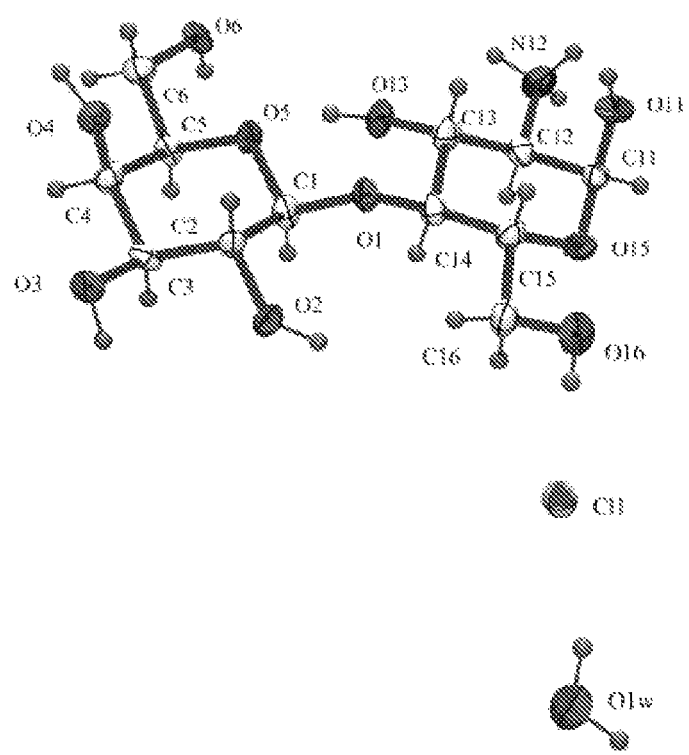
FIG. 1 shows the X-ray structure of α-lactosamine hydrochloride monohydrate.

A crude anomeric mixture of lactosamine hydrochloride can be prepared by using literature methods.[1-7] Different methods of preparation provide different purities of the crude mixture. However, all the expected impurities and side products present in the reaction mixtures obtained by the different methods are found to dissolve in aqueous alcohols at 40-100° C. temperatures. Stirring a solution of the crude mixture in a solvent or mixture of solvents as set out above at between −5 and 30° C. initiates the crystallization of α-lactosamine hydrochloride. Filtration, washing of the crystals with EtOH or iso-propanol, followed by a drying process at room temperature or higher temperatures provides high purity α-lactosamine hydrochloride monohydrate with a melting point of 174° C.

Alternatively, the crude lactosamine hydrochloride can be dissolved in water at 40-100° C. and subsequently the at least one water miscible solvent is added. Crystallization of α-lactosamine hydrochloride starts upon cooling and stirring.

Examples

Procedure 1:

1.5 kg Crude anomeric mixture of lactosamine hydrochloride obtained according to literature procedures' was dissolved in warm water (1.5 L, 50° C.). Ethanol (4 L) was added to the mixture over a period of 30 min. Then the mixture was cooled down to 0° C. and stirred for 8 h. The white crystals were collected by filtration and washed with ethanol (200 mL). Yield: 1.3 kg pure alpha anomer.

Procedure 2:

100 g crude anomeric mixture of lactosamine hydrochloride obtained according to literature procedures[7] was dissolved in warm water (100 mL, 50° C.). i-Propanol (250 mL) was added to the mixture over a period of 10 min. Then the mixture was cooled down to 0° C. and stirred for 8 h. The white crystals were collected by filtration and washed with i-propanol (20 mL). Yield: 85 g pure alpha anomer.

Procedure 3:

100 g crude anomeric mixture of lactosamine hydrochloride obtained according to literature procedures[7] was dissolved in warm water (100 mL, 50° C.). The solution was added to acetone (1 L) obtaining a white precipitate. This powder was redissolved in water (90 mL) and i-propanol (220 mL) added to the mixture over a period of 10 min. Then the mixture was cooled down to 0° C. and stirred for 8 h. The white crystals were collected by filtration and washed with i-propanol (20 mL). Yield: 82 g pure alpha anomer.

Procedure 4:

100 g crude anomeric mixture of lactosamine hydrochloride obtained according to literature procedures[7] was dissolved in warm water (100 mL, 50° C.). The solution added to acetone (1 L) obtaining a white precipitate. This powder was redissolved in water (90 mL) and ethanol (300 mL) added to the mixture over a period of 10 min. Then the mixture was cooled down to 0° C. and stirred for 8 h. The white crystals were collected by filtration and washed with ethanol (20 mL). Yield: 78 g pure alpha anomer.

Procedure 5:

100 g crude anomeric mixture of lactosamine hydrochloride obtained according to literature procedures[7] was dissolved in warm water (100 mL, 50° C.). The solution was added to acetone (1 L) obtaining a white precipitate. This powder was redissolved in water (90 mL) and a mixture of ethanol and i-propanol (8% i-propanol, 220 mL) was added to the mixture over a period of 10 min. Then the mixture was cooled down to 0° C. and stirred for 8 h. The white crystals were collected by filtration and washed with the solvent mixture (20 mL). Yield: 80 g pure alpha anomer.

Procedure 6:

100 g crude anomeric mixture of lactosamine hydrochloride obtained according to literature procedures'[ ] was dissolved in warm water (100 mL, 50° C.). A mixture of ethanol and i-propanol (8% i-propanol, 250 mL) was added to the mixture over a period of 10 min. Then the mixture was cooled down to 0° C. and stirred for 8 h. The white crystals were collected by filtration and washed with the solvent mixture (20 mL). Yield: 88 g pure alpha anomer.

Procedure 7:

100 g alpha lactosamine hydrochloride obtained according to procedures above was dehydrated under high-vacuum (1-10 mbar) at the temperature of 55° C. resulting in 95 g dehydrated pure alpha anomer.

Procedure 8:

100 g alpha lactosamine hydrochloride obtained according to procedures above was dehydrated under high-vacuum (1-10 mbar) at the temperature of 75° C. resulting in 95 g dehydrated pure alpha anomer.

Procedure 9:

100 g alpha lactosamine hydrochloride obtained according to procedures above was dehydrated under high-vacuum (10-15 mbar) at the temperature of 40° C. resulting in 95 g dehydrated pure alpha anomer.

Procedure 10:

100 g alpha lactosamine hydrochloride obtained according to procedures above was dehydrated under high-vacuum (10-15 mbar) at the temperature of 75° C. resulting in 95 g dehydrated pure alpha anomer.

Procedure 11:

100 g alpha lactosamine hydrochloride obtained according to procedures above was dehydrated under high-vacuum (20-50 mbar) at the temperature of 95° C. resulting in 94 g dehydrated pure alpha anomer.

Procedure 12:

100 g alpha lactosamine hydrochloride obtained according to procedures above was dehydrated under high-vacuum (50-100 mbar) at the temperature of 120° C. resulting in 94 g dehydrated pure alpha anomer.

X-Ray Crystallography

Lactosamine hydrochloride sample was made according the present invention for single crystal X-ray diffraction studies. No crystal structure of lactosamine hydrochloride was published before. However, X-ray structure of the N-acetyl-lactosamine is known.

Applied Investigation i, Single crystal growing ii, Single crystal X-ray diffraction data collection iii, Solution of the structure iv, Analysis of the structure and hydrogen bond network.

v. Calculation of powder diffraction data vi. Powder data collection

Single crystals suitable for X-ray diffraction measurement could be grown by layering methanol onto water solution of lactosamine hydrochloride. This is carried out by preparing a saturated aqueous solution of lactosamine hydrochloride, filtering the solution to remove any remaining solid lactosamine hydrochloride, and then adding a small volume of water followed by careful addition of methanol.

A rather small colorless prism crystal was chosen for the measurement and fixed on the loop using perfluorinated paraffin oil. Structural data were reliable and the results are acceptable for scientific publication and/or patenting.

X-Ray Structure Determination

Colorless prism crystal (0.08×0.05×0.02 mm) of $C_{12}H_{26}N_1Cl_1O_{11}$, M=395.79, monoclinic crystal system, a=4.7931(8) Å, b=13.5508(19)Å, c=13.2816(19)Å, β=93.97(1)°, V=860.6(2)Å$^3$, Z=2, space group: P2$_1$, $\rho_{calc}$=1.527 g cm$^{-3}$. Data were collected at 110(1) K, Bruker-GADDS multiwire proportional diffractometer, Cu Kα radiation λ=1.54184 Å, $\theta_{max}$=63.3°, 6882 measured, 2059 independent reflections of which 1793 reflections were unique with I>2σ(I). Raw data was evaluated using the FRAMBO software, the structure was solved using the SIR-92 software and refined on F$^2$ using SHELX-97 program, publication material was prepared with the WINGX-97 suite, R(F)=0.061 and wR(F$^2$)= 0.156 for 2509 reflections, 254 parameters, 10 restraints. Residual electron density: 0.33/−0.33 e/Å$^3$. Hydrogen atoms at carbon atoms were placed into geometric position while other hydrogen atoms could be found at the difference electron density map. Distance of these hydrogen atoms to the respective oxygen or nitrogen was constrained. Coordinates of hydrogen atoms were allowed to refine within a short range to the donor atom. Position of the hydrogens on the amino group was found using the riding model and their distance to the nitrogen atom was fixed. Because of the extensive hydrogen bond network, alternative positions for some of these hydrogen atoms are possible. Full data and the structure determined therefrom are shown in FIGS. 1 and 2.

Figure 3A:
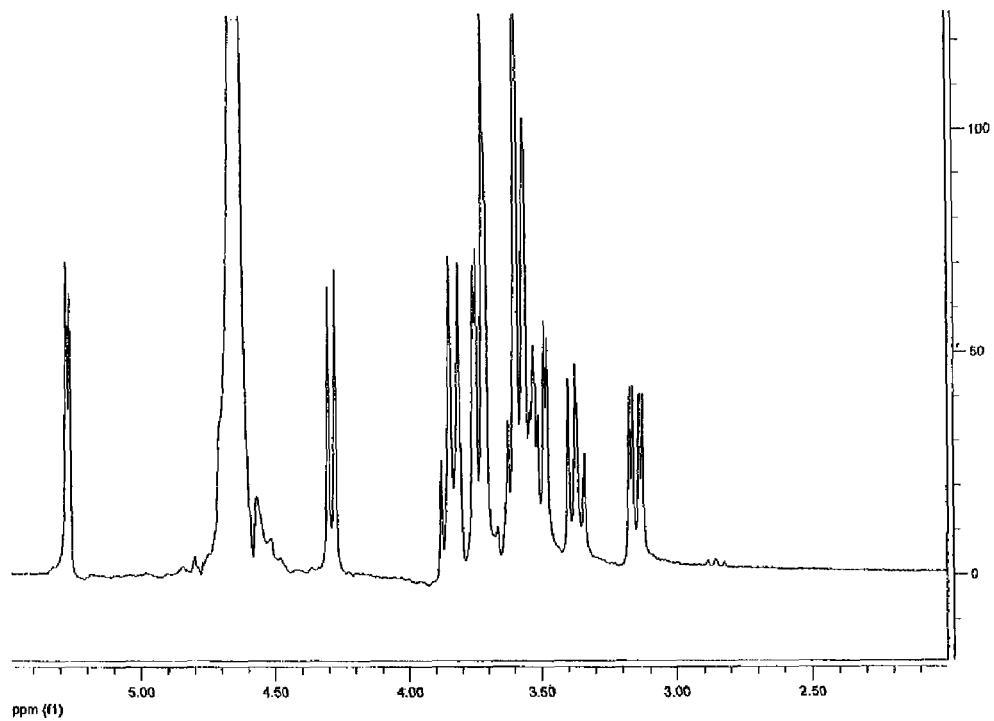
FIG. 3 shows the $^1$H NMR spectrum of α-lactosamine hydrochloride monohydrate in $D_2O$ immediately on preparation of the sample (3A), and a day later (3B).
Figure 3B:
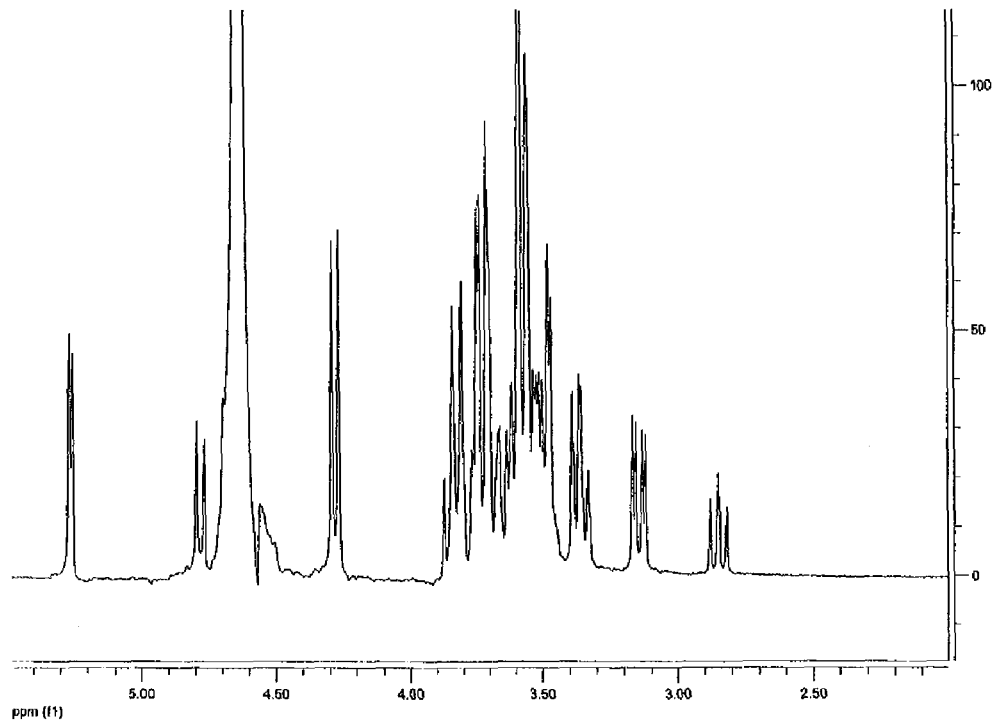

1H-NMR Structure Determination 10 mg pure α-lactosamine hydrochloride was dissolved in 700 μL D$_2$O, then 1H-NMR spectrum was recorded immediately. A second 1H-NMR spectra was recorded a day later, by which time the clean substance had already anomerized. On first spectrum (FIG. 3, above) at 5.26 ppm the H-1 and at 4.29 ppm the H-1' can be seen. On the second spectrum (FIG. 3, below) next to the alpha anomer already the beta appears. At 4.78 ppm H-1-beta and at 2.85 ppm H-2-beta can be seen. This experiment shows that the starting material is a clean anomer, which anomerizes at room temperature within one day.

REFERENCES

1. Oligosaccharides as antitumor drugs and health foods. Misawa, Yoshitomo; Kikuchi, Kazuaki; Hosomi, Osamu. (Yaizu Suisan Kagaku Industry Co., Ltd., Japan). Jpn. Kokai Tokkyo Koho (2004), 16 pp. CODEN: JKXXAF JP 2004352673
2. An Exceptionally Simple Chemical Synthesis of O-Glycosylated D-Glucosamine Derivatives by Heyns Rearrangement of the Corresponding O-Glycosyl Fructoses. Stuetz, Arnold E.; Dekany, Gyula; Eder, Brigitte; Illaszewicz, Carina; Wrodnigg, Tanja M. Institut fuer Organische Chemie, Glycogroup, Technische Universitaet Graz, Graz, Austria. Journal of Carbohydrate Chemistry (2003), 22(5), 253-265.
3. A Unique Chemoenzymic Synthesis of α-Galactosyl Epitope Derivatives Containing Free Amino Groups: Efficient Separation and Further Manipulation. Fang, Jianwen; Chen, Xi; Zhang, Wei; Wang, Jianqiang; Andreana, Peter R.; Wang, Peng George. Department of Chemistry, Wayne State University, Detroit, Mich., USA. Journal of Organic Chemistry (1999), 64(11), 4089-4094.
4. The Heyns rearrangement revisited: an exceptionally simple two-step chemical synthesis of D-lactosamine from lactulose. Wrodnigg, Tanja M.; Stutz, Arnold E. Institut fur Organische Chemie der Technischen Universitat, Graz, Austria. Angewandte Chemie, International Edition (1999), 38(6), 827-828.
5. Chemical and enzymic synthesis of glycoconjugates 3: synthesis of lactosamine by thermophilic galactosidase catalyzed galactosylation on a multigram scale. Fang, Jianwen; Xie, Wenhua; Li, Jun; Wang, Peng George. Department Chemistry, Wayne State University, Detroit, Mich., USA. Tetrahedron Letters (1998), 39(9), 919-922.
6. Synthesis of 2-acetamidolactose. Kuhn, Richard; Kirschenlohr, Werner. Univ. Heidelberg, Germany. Chemische Berichte (1954), 87 1547-52
7. Process for the large-scale preparation of N-acetyllactosamine, lactosamine, lactosamine salts and lactosamine-containing oligosaccharides. Dekany, Gyula; Agoston, Karoly; Bajza, Istvan; Boejstrup, Marie; Kroeger, Lars. (Glycom Aps, Den.). PCT Int. Appl. (2007), 44 pp. CODEN: PIXXD2 WO 2007104311
8. Method for the preparation of aminosugars. Spreitz, Josef; Sprenger, Friedrich. (Austria). Austrian Pat. Appl. [Pre-Grant] (2007), 23 pp. CODEN: ATXXAD AT 503400 A1 20071015

The invention claimed is:

1. A purified α-lactosamine hydrochloride, in the form of the crystalline monohydrate as shown in Formula 1, comprising less than 5% by weight β-lactosamine hydrochloride

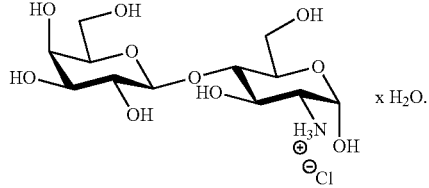

Formula 1

2. The α-lactosamine hydrochloride as claimed in claim 1, comprising less than 1% by weight of β-lactosamine hydrochloride.

3. The α-lactosamine hydrochloride as claimed in claim 1, comprising less than 0.1% by weight of β-lactosamine hydrochloride.

4. A composition comprising the α-lactosamine hydrochloride of claim 1.

5. A food product, beverage or functional food supplement comprising the α-lactosamine hydrochloride of claim 1.

* * * * *

UNITED STATES PATENT AND TRADEMARK OFFICE
CERTIFICATE OF CORRECTION

PATENT NO.         : 8,796,434 B2  
APPLICATION NO.    : 13/054314  
DATED              : August 5, 2014  
INVENTOR(S)        : Gyula Dekany et al.

Page 1 of 1

It is certified that error appears in the above-identified patent and that said Letters Patent is hereby corrected as shown below:

On Title Page, Item (75) Inventors, Line 4
replace "Ignacio Fegueroa Pérez,"
with --Ignacio Figueroa Pérez--.

On Title Page, Item (73) Assignee
replace "KGS. Lyngby (DK)"
with --Kgs. Lyngby (DK)--.

Signed and Sealed this
Fourteenth Day of October, 2014

Michelle K. Lee
*Deputy Director of the United States Patent and Trademark Office*